US009804029B2

(12) United States Patent
Sonehara et al.

(10) Patent No.: US 9,804,029 B2
(45) Date of Patent: Oct. 31, 2017

(54) MICROSPECTROSCOPY DEVICE

(71) Applicant: HITACHI HIGH-TECHNOLOGIES CORPORATION, Tokyo (JP)

(72) Inventors: Tsuyoshi Sonehara, Tokyo (JP); Hiromi Kusaka, Tokyo (JP); Akira Fujii, Tokyo (JP); Shuhei Yamamoto, Tokyo (JP); Takeshi Ooura, Tokyo (JP); Michiru Fujioka, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/120,792

(22) PCT Filed: Jan. 16, 2015

(86) PCT No.: PCT/JP2015/051000
§ 371 (c)(1),
(2) Date: Aug. 23, 2016

(87) PCT Pub. No.: WO2015/133176
PCT Pub. Date: Sep. 11, 2015

(65) Prior Publication Data
US 2017/0023409 A1  Jan. 26, 2017

(30) Foreign Application Priority Data

Mar. 5, 2014  (JP) ................. 2014-042263

(51) Int. Cl.
*G01J 3/30* (2006.01)
*G01J 3/42* (2006.01)
(Continued)

(52) U.S. Cl.
CPC ................ *G01J 3/44* (2013.01); *G01J 3/021* (2013.01); *G01J 3/0208* (2013.01);
(Continued)

(58) Field of Classification Search
CPC ........ G01J 3/0208; G01J 3/021; G01J 3/0229; G01J 3/0248; G01J 3/10; G01J 3/44;
(Continued)

(56) References Cited

U.S. PATENT DOCUMENTS

| 5,442,438 A | 8/1995 | Batchelder et al. |
| 6,452,145 B1 * | 9/2002 | Graves ...................... G01J 9/00 |
| | | 250/201.9 |

(Continued)

FOREIGN PATENT DOCUMENTS

| JP | 10-239037 A | 9/1998 |
| JP | 2003-526814 A | 9/2003 |

(Continued)

OTHER PUBLICATIONS

International Search Report of PCT/JP2015/051000 dated Apr. 14, 2015.

*Primary Examiner* — Sunghee Y Gray
(74) *Attorney, Agent, or Firm* — Mattingly & Malur, PC

(57) ABSTRACT

With a microspectroscopy device provided with an objective lens with a high numerical aperture, a defocus arises from thermal drift, etc., necessitating auto-focusing. Conventional auto-focus based on through-focus image acquisition takes time, and thus, it cannot be applied to continuous measurement over a long time wherein high-speed sampling is carried out. The present invention addresses this problem by having a defocus-sensing beam that has either defocus or astigmatism fall incident on the objective lens. Since how the image of the spot of the beam for defocus sensing blurs differs depending on the orientation of the defocus, real-time detection of the amount and orientation of defocus becomes possible, and high-speed realtime auto-focus becomes possible.

4 Claims, 5 Drawing Sheets

(51) Int. Cl.

| | | |
|---|---|---|
| *G01J 3/24* | (2006.01) | |
| *G01J 3/44* | (2006.01) | |
| *G02B 7/28* | (2006.01) | |
| *G02B 7/32* | (2006.01) | |
| *G01N 21/65* | (2006.01) | |
| *G02B 21/36* | (2006.01) | |
| *G01N 21/64* | (2006.01) | |
| *G01J 3/02* | (2006.01) | |
| *G01J 3/10* | (2006.01) | |
| *G02B 21/00* | (2006.01) | |
| *G02B 21/16* | (2006.01) | |
| *G02B 21/24* | (2006.01) | |
| *G02B 27/14* | (2006.01) | |

(52) U.S. Cl.
CPC ........... *G01J 3/0229* (2013.01); *G01J 3/0248* (2013.01); *G01J 3/10* (2013.01); *G01J 3/4406* (2013.01); *G01N 21/6458* (2013.01); *G01N 21/65* (2013.01); *G02B 7/28* (2013.01); *G02B 7/32* (2013.01); *G02B 21/0004* (2013.01); *G02B 21/16* (2013.01); *G02B 21/244* (2013.01); *G02B 21/36* (2013.01); *G02B 21/365* (2013.01); *G02B 27/141* (2013.01)

(58) Field of Classification Search
CPC ... G01J 3/4406; G01N 21/6458; G01N 21/65; G02B 21/0004; G02B 21/16; G02B 21/244; G02B 21/36; G02B 21/365; G02B 27/141
USPC .......................................... 356/317–323, 326
See application file for complete search history.

(56) References Cited

U.S. PATENT DOCUMENTS

| | | |
|---|---|---|
| 6,974,938 B1 | 12/2005 | Leblans et al. |
| 2006/0258942 A1* | 11/2006 | Van Beek ............ A61B 5/0059 600/477 |
| 2007/0103687 A1 | 5/2007 | Okazaki |
| 2013/0070076 A1 | 3/2013 | Kuster |
| 2013/0176563 A1 | 7/2013 | Ozawa et al. |

FOREIGN PATENT DOCUMENTS

| | | |
|---|---|---|
| JP | 2004-078069 A | 3/2004 |
| JP | 4914715 B2 | 4/2012 |
| JP | 2013-065015 A | 4/2013 |

* cited by examiner

US 9,804,029 B2

MICROSPECTROSCOPY DEVICE

TECHNICAL FIELD

The present invention relates to a microspectroscopy device which is a combination of an optical microscope and a spectroscope. The present invention is useful for Raman microspectroscopy and also useful for laser induced fluorescence spectroscopy in addition. The present invention is particularly useful for applications requiring long-term continuous measurement such as determination of the DNA base sequence based on the Raman microspectroscopy, etc.

BACKGROUND ART

In PTL 1, a device for analyzing a biopolymer by irradiating the biopolymer passing through a nanopore with light to generate Raman scattering light, and measuring the light is described.

For the analysis of the Raman scattering light, a microspectroscopy device (a combination of a microscope and a spectroscopic optical system) called a Raman microscope is used, as described in PTL 2. In a Raman microscope, in order to observe weak Raman scattering light with high sensitivity and high resolution, an objective lens with high numerical aperture of nearly one or more is often used. In a microscope with such a high numerical aperture, the depth of field becomes submicron. Maintaining the distance between the sample and the objective lens stably for a long time at this level is difficult with only mechanical fixing, due to thermal expansion or the like. In the case of a single measurement such as a conventional microscope measurement, the focus can be adjusted for each measurement. However, at the time of long-term continuous measurement while a large biopolymer such as DNA is passing through a nanopore, performance of normal focusing becomes an interruption of the measurement and is not preferable. For such measurements, a real-time defocus correction (autofocus) is preferred.

In conventional Raman microscopes, one excitation light beam is focused on one spot on a sample substrate by an objective lens to observe the light emission image on the spot. By observing the image on the spot, the occurrence of defocus can be detected but it is difficult to detect the direction.

Therefore, in a normal focusing, while measuring the image, shifting of the distance between the sample and the objective lens back and forth around the present position (acquisition of through-focus image) is necessary. This can be time consuming and is not suitable for real-time auto focus in continuous measurement.

CITATION LIST

Patent Literature

PTL 1: US 2013/0,176,563 A
PTL 2: U.S. Pat. No. 5,442,438

SUMMARY OF INVENTION

Technical Problem

In microspectroscopy device equipped with a high numerical aperture objective lens, a high-speed real-time autofocus which enables continuous measurement is achieved over a long time for which the defocus cannot be avoided due to thermal expansion or the like.

Solution to Problem

A defocus-sensing beam having defocus or astigmatism is incident on the objective lens. Since the blur of the spot image of such a defocus-sensing beam is different depending on the direction of defocus, it becomes possible to detect the amount and direction of defocus in real time, thereby high-speed real-time autofocusing is enabled.

Advantageous Effects of Invention

Long-term continuous analysis of large polymers such as DNA passing through a nanopore, that is, base sequence determination for example becomes possible. Further, when performing multi-point measurement for one sample substrate, the tilt of the substrate can be detected.

DESCRIPTION OF EMBODIMENTS

Hereinafter, embodiments of the present invention will be described with reference to the accompanying drawings.

Figure 1:
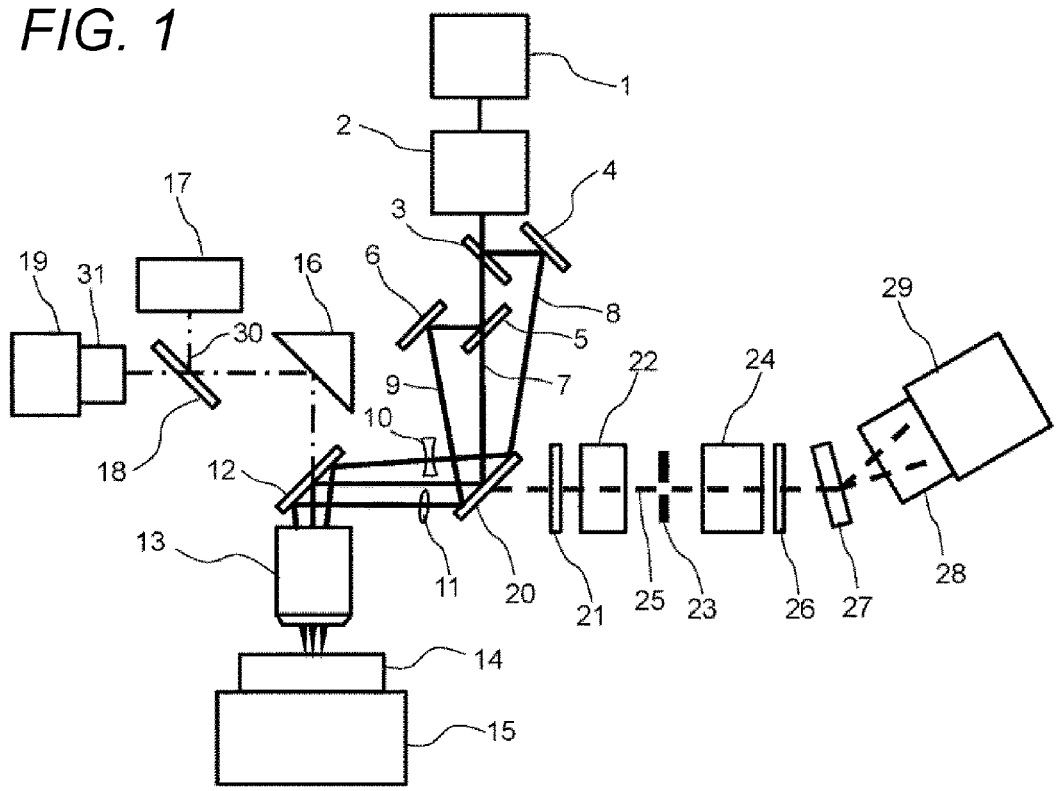
FIG. 1 is a configuration diagram showing a first embodiment of the present invention.

FIG. 1 is a configuration diagram showing a first embodiment of the present invention. A beam emitted from an excitation laser light source 1 is converted into a parallel beam with a large width by a beam expander 2. The excitation laser light source 1 in this embodiment is for a near-infrared laser having a wavelength of 785 nm. The output beam of the beam expander 2 is split by beam splitters 3 and 5 into a total of three beams of a sample excitation beam 7 and defocus-sensing beams 8 and 9.

These three beams are input to an objective lens 13 by mirrors 4 and 6 and dichroic mirrors 20 and 12, and are condensed in the vicinity of the surface of a sample 14. As shown in FIG. 1, the defocus-sensing beam 8 is divided from the sample excitation beam 7 by the beam splitter 3 and is input to the objective lens 13 through the mirror 4, the dichroic mirror 20 and the dichroic mirror 12 in this order, and then is focused in the vicinity of the surface of the sample 14. Further, the defocus-sensing beam 9 is divided from the sample excitation beam 7 by the beam splitter 5, and is reflected by the dichroic mirror 12 to be input to the objective lens 13 after passing through the mirror 6 and the dichroic mirror 20 in this order, thereby being condensed in the vicinity of the surface of the sample 14.

The sample 14 is fixed on an XYZ stage 15, and the observation position can be changed by the XY stage and the focus can be adjusted by the Z stage. The defocus-sensing beam 8 is subjected to insertion of a concave lens 10 and enters the objective lens 13 as a divergent beam. Instead of the concave lens 10, the convex lens having a short focal length and a focal point in front of the objective lens can similarly allow the beam 8 to be incident on the objective lens 13 as a divergent beam. The defocus-sensing beam 9 is subjected to insertion of a convex lens 11 and is incident on the objective lens 13 as a convergent beam.

The light scattered on the sample surface is collected by the objective lens 13, and formed into a substantially parallel beam, and then reflected by the dichroic mirror 12 to be transmitted through the dichroic mirror 20. The Rayleigh scattering light component is blocked by a filter 21, and only the Raman scattered light component is focused on a pinhole 23 by a first imaging lens 22. The Raman scattered light other than the light from the light condensing spot of the sample excitation beam is blocked by the pinhole 23.

The light transmitted through the pinhole 23 is collimated by a relay lens 24, and is dispersed by a diffraction grating 27 after the remaining Rayleigh scattering light component is blocked by a filter 26, and then the spectrum thereof is imaged onto the imaging device for detecting Raman scattering light by a second imaging lens 28. The filters 21 and 26 are band-pass filters which allow the light having a wavelength between 792 nm and 935 nm to transmit therethrough and block the others.

Visible white light emitted from a white light source 17 is reflected by a beam splitter 18 and a prism 16, and is introduced to the objective lens 13 after being transmitted through the dichroic mirror 12, thereby illuminating the surface of the sample 14. The scattered light of visible white light from the sample is collected by the objective lens 13, and travels reversely along the illumination light path, and then is focused on a monitoring imaging device 19 by a lens 31 after passing through the beam splitter 18. The dichroic mirror 12 basically reflects near-infrared light and transmits light of the visible range, but also transmits about 0.1% of near-infrared laser light. The spot intensity of the near-infrared laser light formed on the sample is much higher than the white light illumination and thus is observed as a bright spot on the monitoring imaging device 19.

Figure 2:
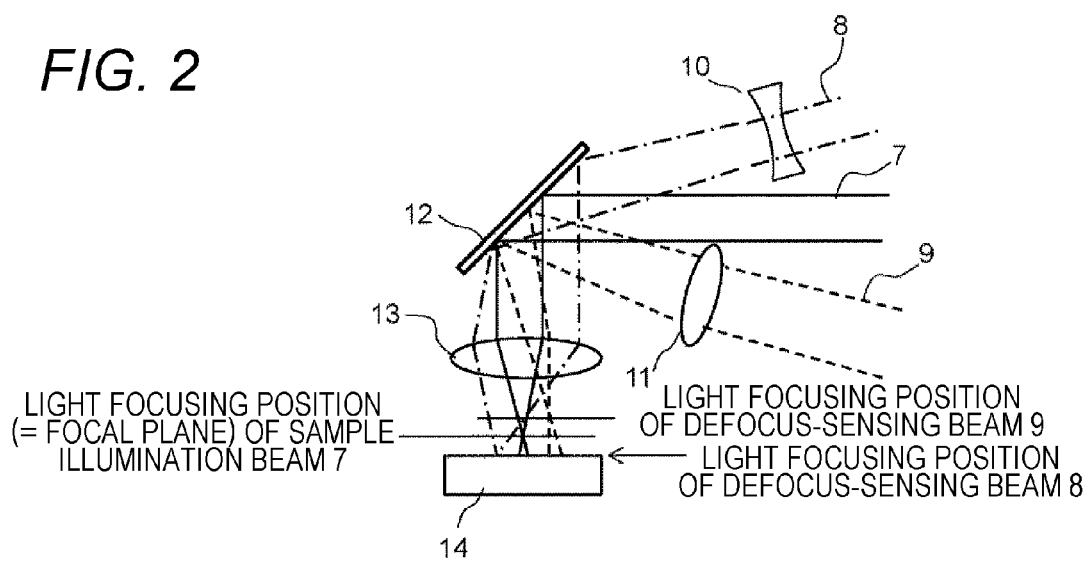
FIG. 2 is an enlarged view of the periphery of an objective lens according to the first embodiment.

FIG. 2 is an enlarged view of the periphery of the objective lens in the present embodiment. The sample excitation beam is a parallel beam, and hence, is focused onto the focal plane of the objective lens 13. This spot is called the spot 0. The defocus-sensing beam 8 is a divergent beam, and therefore, is focused farther than the focal plane as viewed from the objective lens. This spot is defined as the spot +. The defocus-sensing beam 9 is a convergent beam, and therefore, is focused closer than the focal plane as viewed from the objective lens. This spot is defined as the spot −. The defocus is defined as a plus defocus when the sample surface is farther than the focal plane as viewed from the objective lens, and as a minus defocus when the sample surface is close to the focal plane. FIG. 2 shows a state of the plus defocus as an example.

Figure 3:
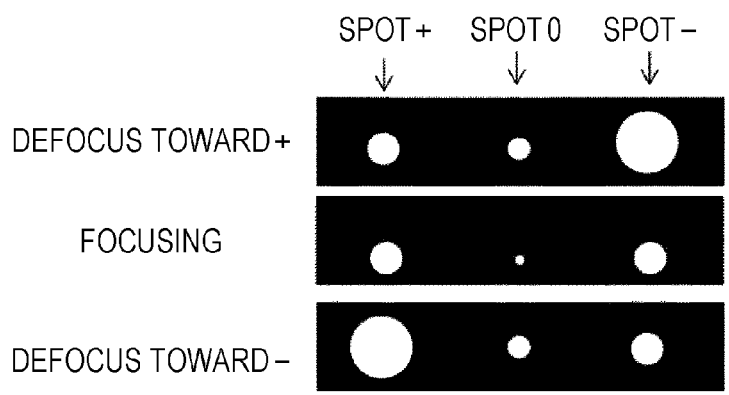
FIG. 3 illustrates the relationship of a spot image and a defocus in the first embodiment.

FIG. 3 schematically shows images of the spot 0, spot + and spot − obtained by the monitoring imaging device 19. In the case of the defocus of +, the spot − becomes larger than the spot + in size, and on the contrary, in the case of defocus of −, the spot + becomes larger than the spot − in size. Therefore, the direction of the defocus can be detected from the magnitude relation between the spot + and the spot −. More quantitatively, the defocus amount can be obtained by ((size of spot −)−(size of spot +))×proportionality constant. The proportionality coefficient can be determined by obtaining a through-focus image once before the actual measurement. Thus, a defocus amount including a sign is obtained from the monitoring camera image, and an excellent focusing state for a long period of time can be maintained without interrupting the measurement, by moving the Z stage in the direction for canceling the amount. In other words, real-time high-speed auto focus is achieved.

Figure 4:
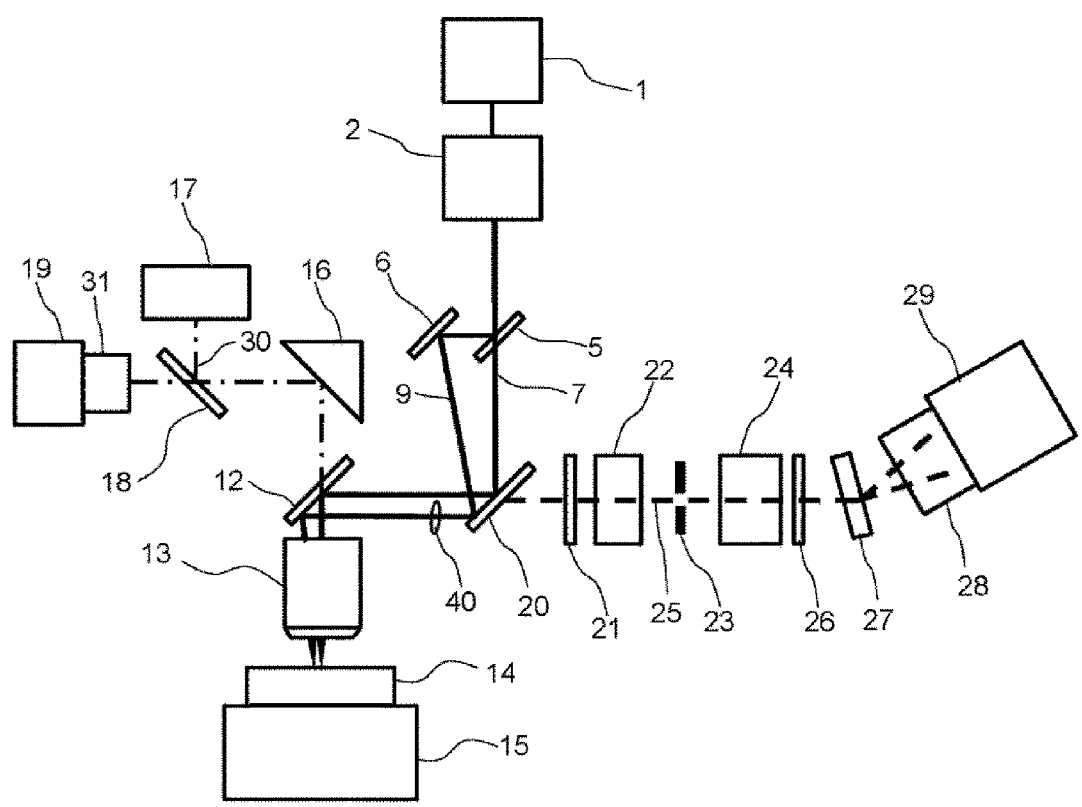
FIG. 4 is a configuration diagram showing a second embodiment of the present invention.
Figure 5:
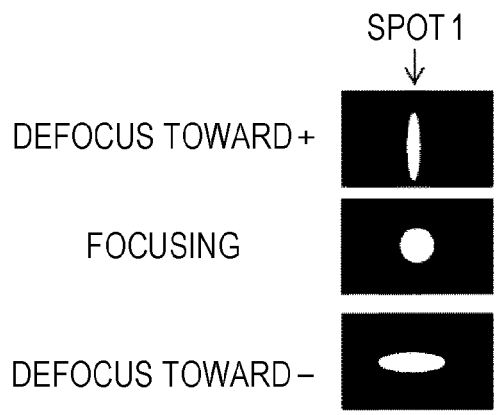
FIG. 5 illustrates the relationship of a spot image and a defocus in the second embodiment.

FIG. 4 is a configuration diagram showing a second embodiment of the present invention. The basic structure of this embodiment is similar to the first embodiment. The laser output beam is split by the beam splitter 5 in this embodiment and the sample excitation beam 7 and one defocus-sensing beam 9 are obtained. A cylindrical lens 40 is inserted into the path of the defocus-sensing beam 9 as a means for generating astigmatism. Of course, the means for generating the astigmatism is not limited to the cylindrical lens 40. The image of the spot (spot 1) of the defocus-sensing beam 9 on the monitoring imaging device in this example is schematically shown in FIG. 5. Due to astigmatism, the spot becomes vertically long in the case of defocus toward +, and horizontally long in the case of the defocus toward −. Therefore, the sign of defocus can be detected from the spot shape. More quantitatively, a high-speed real-time auto focus can be achieved similarly to the first embodiment, by the feedback operation to the Z stage while employing the value ((vertical size of spot 1)−(horizontal size of spot 1))× proportionality constant as the defocus amount. As a specific effect of the present embodiment, only one defocus-sensing beam is required as its advantage.

Figure 6:
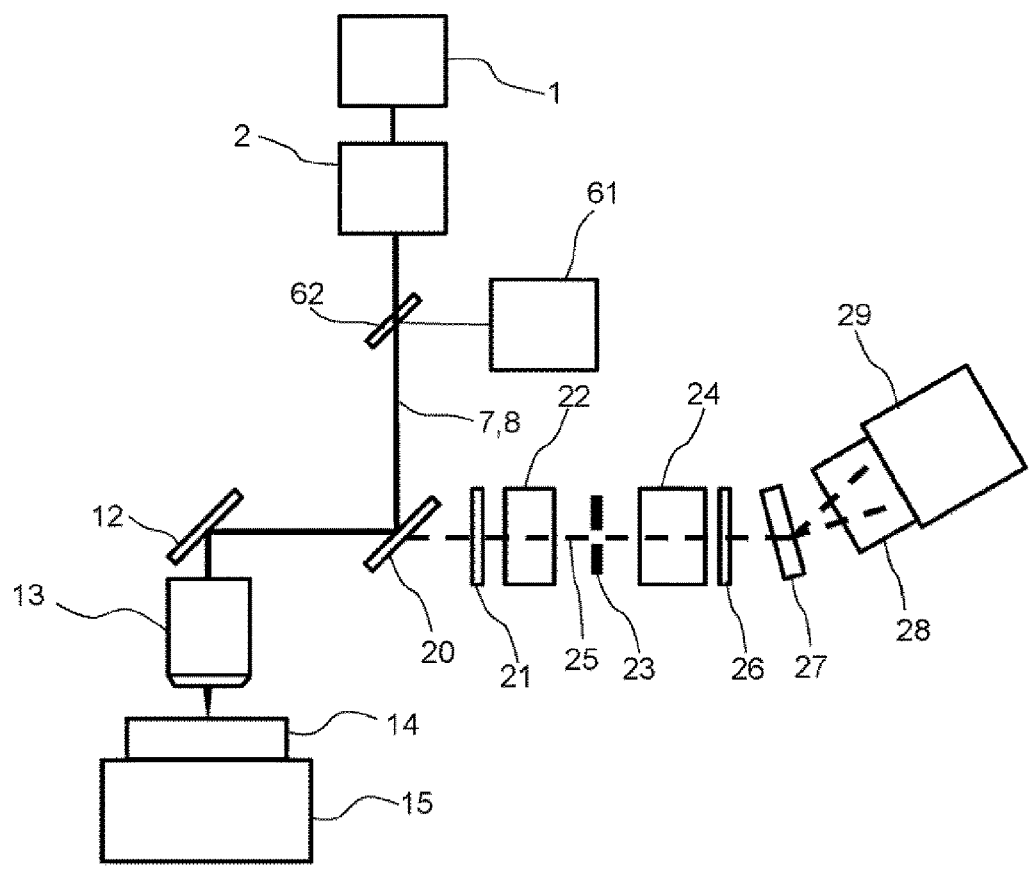
FIG. 6 is a configuration diagram showing a third embodiment of the present invention.

FIG. 6 is a configuration diagram showing a third embodiment of the present invention. Also in this embodiment, the basic configuration is similar to the first embodiment. In the present embodiment, in addition to the laser light source 1 of a wavelength of 785 nm for sample illumination, a laser light source 61 of a wavelength of 920 nm for the defocus sensing exclusive use is provided, and the output beam of 1 and the output beam of the laser light source 61 are combined by a dichroic mirror, and then the optical axes are agreed with each other for illuminating the sample 14. The 920 nm laser 61 is a semiconductor laser, and the output beam itself has astigmatism. The purpose of the present embodiment is to observe Raman scattering light of the wave number range from 100 $cm^{-1}$ to 1800 $cm^{-1}$ from the sample 14 excited at 785 nm. Since 920 nm (1890 $cm^{-1}$) is outside this range, an image of 920 nm spot scattered light is observed on the outside of the Raman spectrum on the imaging device 29 for Raman scattering light observation. The 920 nm laser 61 is a semiconductor laser, and the output beam itself has astigmatism. Accordingly, an image of the 920 nm spot similar to in FIG. 5 can be obtained in accordance with the defocus in the imaging device 29, and high-speed real-time autofocus can be achieved similarly to the second embodiment. In the present embodiment, a monitoring imaging device and an optical system for the device can be omitted.

Figure 7:
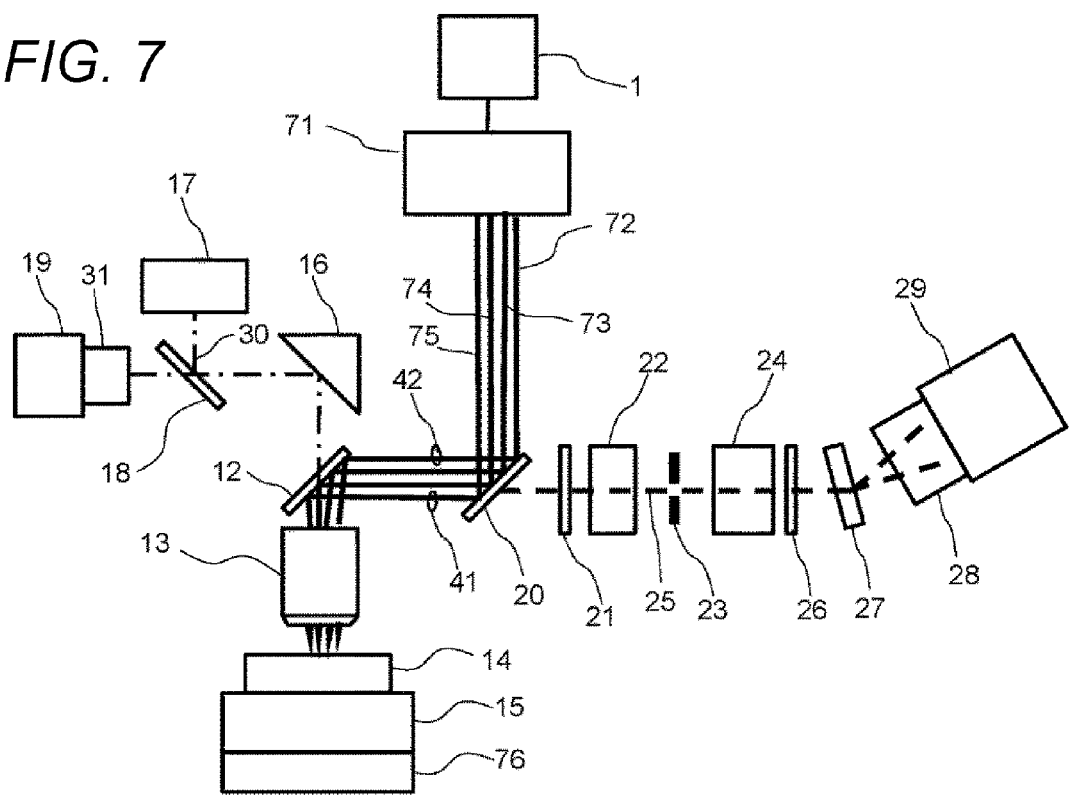
FIG. 7 is a configuration diagram showing a fourth embodiment of the present invention.

FIG. 7 is a configuration diagram showing a fourth embodiment of the present invention. Also in this embodiment, the basic configuration is similar to the first embodiment. An output beam of the laser light source 1 is branched into four by a multi-beam generator 71 and two of them (73 and 74) are employed as the sample illumination beam and the other two (72 and 75) are employed as defocus-sensing beams in the present embodiment. Cylindrical lenses 41 and 42 are inserted in the paths of the defocus-sensing beams 72 and 75 respectively, and then the astigmatism is given. In this embodiment, two spots for Raman spectrum observation and two defocus-sensing spots, that is, a total of four spots are formed in a straight line on the sample 14. The defocuses of the two spots are determined similarly to the second embodiment and, as a result, the tilt of the sample surface can be obtained. A tilt correction stage 76 is provided in addition to the XYZ stage 15 to correct the tilt in accordance with the tilt determined from the spot image of the defocus-sensing beam in the present embodiment. Then, the defocus in the Z direction is corrected by the movement of the Z stage. As a result, focuses are adjusted on both of the two spots for Raman spectrum observation, and Raman spectra of two points of the sample 14 can be observed with high sensitivity and high resolution simultaneously.

In the present embodiment, although for convenience of illustration, a tilt of only one direction is detected by two defocus-sensing spots, tilts in two directions of the sample surface can be detected by arranging three or more defocus-sensing spots which are not on the same straight line. By providing a biaxial tilt correction stage, both the tilts are corrected, and it is also possible to simultaneously adjust the focuses of all the three or more two-dimensionally arranged spots for Raman observation.

Figure 8:
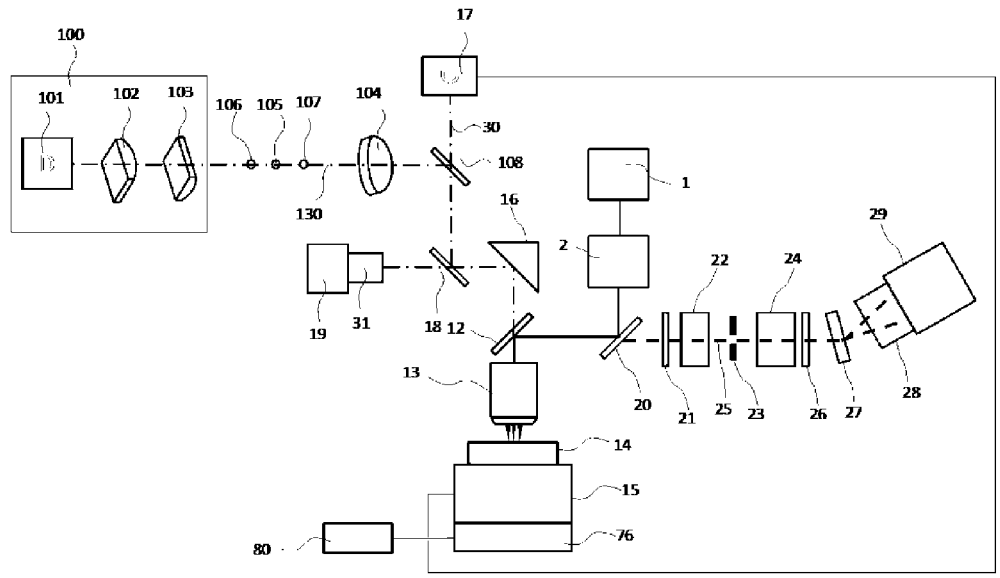
FIG. 8 is a configuration diagram showing a fifth embodiment of the present invention.

FIG. 8 is a configuration diagram showing a fifth embodiment of the present invention. Also in this embodiment, the basic configuration is similar to the first embodiment. The same numbers are given to the same parts and detailed description thereof will be omitted. In the present embodiment, a light source unit 100 for exclusive use for generating a defocus-sensing beam 130 is provided. The light source unit 100 is composed of a laser light source 101, and cylindrical lenses 102 and 103. As the wavelength of the laser light source 101, any wavelength is acceptable only if the wavelength is shorter than that of the excitation laser light source 1 and may be 633 nm of visible light for example. The cylindrical lenses 102 and 103 are arranged such that the surfaces including curvatures are perpendicular to each other, and a focal point 106 of the cylindrical lens 102 and a focal point 107 of the cylindrical lens 103 are positioned symmetrically with a focal point 105 of a tube lens 104 as the center. With this arrangement, astigmatism having astigmatic difference equal to the distances to the focal points 106 and 107 from the focal point 105 as the midpoint is given to the defocus-sensing beam 130. The defocus-sensing beam 130 passes through the same optical path as a white light 30 and enters the objective lens 13 after being combined with the white light 30 by a beam splitter 108. The imaging lens 104 is arranged so that the focal point 105 and the focal point of the objective lens 13 (not shown) are conjugated. Therefore, the focusing point of the objective lens 13 can be the midpoint of the astigmatic difference of the defocus-sensing beam 130 similarly to the focal point 105. An image formed on the monitoring imaging device 19 by the defocus-sensing beam 130 becomes vertically long when defocused toward + from the focusing point of the objective lens 13, and becomes horizontally long when defocused toward −, in the same manner as in FIG. 5. A controller 80 has a function of calculating the direction and amount of the defocus from the shape of the image formed on the monitoring imaging device 19 and of sending a feedback control signal to the XYZ stage 15. The XYZ stage 15 allows the following motion of the Z stage based on the given feedback control signal.

Thus, also in this embodiment, it is possible to detect the sign of defocus from the shape of the spot and to achieve a high-speed real-time autofocus.

Here, a description of a method of determining the focus-sensing range will be given. An astigmatic difference amount D with the focal point 105 as the center and an astigmatic difference amount d with the focusing point of the objective lens 13 at the center have a relationship of longitudinal magnification, by using the magnification M of the tube lens 104 and the objective lens 13. The astigmatic difference amount d corresponds to a defocus-sensing range. According to the required defocus-sensing range (astigmatic difference amount d), the focal distances, arrangement and magnification M of the cylindrical lenses 102 and 103 may be selected such that $d=D/M^2$.

Also in this embodiment, the object is to observe Raman scattering light of the wave number range from 100 $cm^{-1}$ to the 1800 $cm^{-1}$ from the sample 14 excited at 785 nm. Since the defocus-sensing beam 130 has a shorter wavelength than the laser light source 1 as described above, most of the power is blocked in the dichroic mirror 12 and the filters 21 and 26. In addition, since the defocus-sensing beam 130 has a shorter wavelength than the excitation light source, that is, smaller than 0 $cm^{-1}$, an image is formed on the outside of the Raman spectrum on the imaging device 29 for Raman scattering observation. Thus, also in this embodiment, there is an advantage that the defocus-sensing beam 130 does not affect the observation of the Raman spectrum.

Figure 9:
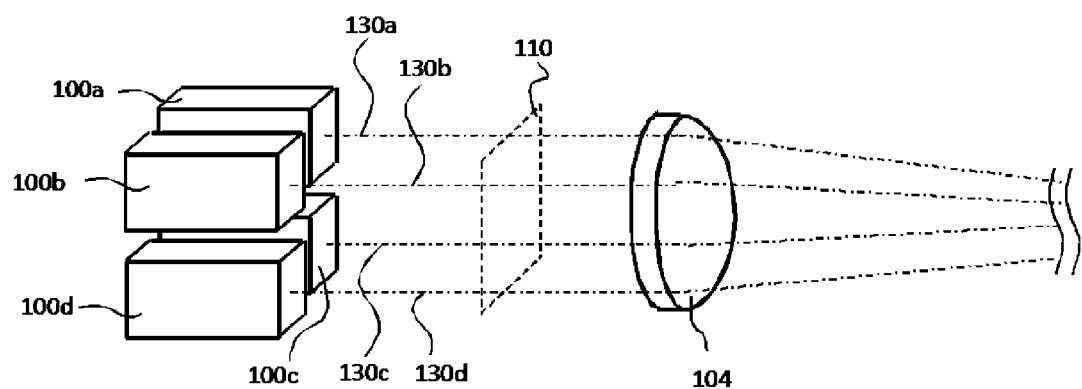
FIG. 9 is a configuration diagram showing a sixth embodiment of the present invention.

FIG. 9 is a configuration diagram showing a sixth embodiment of the present invention. This embodiment is obtained by replacing the light source unit 100 of the fifth embodiment with light source units 100a, 100b, 100c and 100d. Only the light source units 100a to 100d and the tube lens 104 are shown by extracting them, and other components are omitted. The light source units 100a to 100d are composed of the same components as the light source unit 100, and there are a single laser light source and two cylindrical lenses (not shown). The surface 110 is a plane which extends through the focal position of the tube lens 104 and is perpendicular to the optical axis of the tube lens 104. The light source units 100a to 100d emit defocus-sensing beams 130a to 130d, respectively. Astigmatism with the surface 110 positioned at the center is given to the defocus-sensing beams 130a to 130d by two cylindrical lenses in the light source units 100a to 100d, similarly to the defocus-sensing beam 130. Then after the defocus-sensing beams 130a to 130d are combined with the white light by the beam splitter and are incident on the objective lens to form a spot on the sample (not shown).

Figure 10:
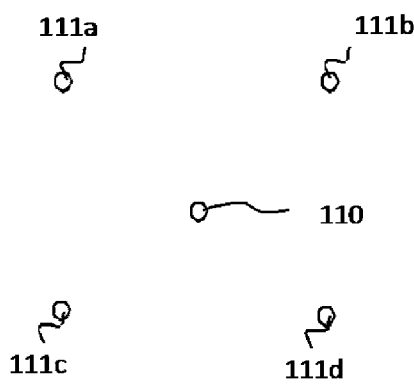
FIG. 10 is a schematic diagram of an image of the sixth embodiment.

FIG. 10 schematically illustrates an image obtained by the imaging device 19. A spot 110 represents an excitation beam, and spots 111a to 111d represent spots formed on the sample by the defocus-sensing beams 130a to 130d respectively. As shown in the figure, the defocus-sensing beams 130a to 130d are characterized by irradiation to positions away from the excitation beam. In the present embodiment, by observing the spots 111a to 111d simultaneously, there is advantage that it is possible not only to detect the defocus but also to detect two-directional tilt of the sample surface simultaneously.

Since the defocus-sensing beams 130a to 130d have shorter wavelengths than the excitation beam, most of the power is blocked by the dichroic mirror 20 and the filters 21 and 26. Furthermore, the defocus-sensing beams are away from the spot position of the excitation beam, and thus are blocked by the pinhole 23. Due to this, most of the effect of defocus-sensing beam on Raman light can be eliminated.

Though the present embodiment is constituted by four defocus-sensing beams, bi-directional tilt may be detected without problems by constituting three defocus-sensing beams whose at least one of spots formed on the sample is arranged on a non-linear line.

In the present embodiment, astigmatism is given to the defocus-sensing beam by two cylindrical lenses. However, they may be one or more cylindrical lenses having functions of two cylindrical lenses, or one or more diffractive elements having functions of two cylindrical lenses.

In the present embodiment, the excitation beam is one in number, but the excitation beam may be even multiple beams without any problems as in the fourth embodiment.

Although a diffraction beam splitter is used as a multi-beam generator in the present embodiment, a conventional beam splitter subjected to a cascade connection may be used as a matter of course.

Although embodiments of the present invention have been described mainly regarding the application to the Raman spectroscopy, the present invention can be similarly applied also to fluorescence spectroscopy.

REFERENCE SIGNS LIST 1 excitation laser light source
2 beam expander
3 beam splitter
4 mirror
5 beam splitter
6 mirror
7 excitation beam
8 defocus-sensing beam
9 defocus-sensing beam
10 concave lens
11 convex lens
12 dichroic mirror
13 objective lens
14 sample
15 XYZ stage
16 prism
17 white light source
18 beam splitter
19 imaging device
20 dichroic mirror
21 filter
22 first imaging lens
23 pinhole
24 relay lens
25 Raman scattering light
26 filter
27 diffraction grating
28 second imaging lens
29 imaging device
30 white light
31 lens
40 cylindrical lens
71 multi-beam generator
72 defocus-sensing beam
73 excitation beam
74 excitation beam
75 defocus-sensing beam
41 cylindrical lens
42 cylindrical lens
76 tilt correction stage
80 controller

The invention claimed is:

1. A microspectroscopy device comprising:
a light source for outputting an excitation beam for exciting a light emission from a sample;
an objective lens for illuminating the sample with the excitation beam;
an imaging device for detecting the light emission from the sample excited by the excitation beam;
a defocus-sensing beam having a wavelength or an optical axis different from a wavelength or an optical axis of the excitation beam incident on the objective lens;
a stage for moving the sample in a direction of an optical axis of the objective lens;
a monitoring imaging device for observing a shape of an image formed on the sample by the defocus-sensing beam having passed through the objective lens; and
a controller for detecting a direction and an amount of defocus from the shape of the image of the defocus-sensing beam and for sending a feedback control signal so as to move the stage to a focus position of the objective lens,
the defocus-sensing beam includes at least two or more defocus-sensing beams,
at least one of the at least two or more defocus-sensing beams is focused by the objective lens at a position closer to the objective lens than a position where the excitation light beam is focused by the objective lens, and at least one of the at least two or more defocus-sensing beams is focused by the objective lens at a position farther from the objective lens than the position where the excitation light beam is focused by the objective lens, and
the microspectroscopy device further comprises a monitoring imaging device for observing the defocus.

2. The microspectroscopy device according to claim 1, comprising at least two beam splitters on an optical path of the excitation light beam, a concave lens on one optical path after splitting, and a convex lens on the other optical path after the splitting, provided to generate the defocus-sensing beam.

3. The microspectroscopy device according to claim 1, wherein the controller detects a tilt of a surface of the sample in at least one or more directions.

4. The microspectroscopy device according to claim 1, comprising a multi-beam generator for generating a plurality of excitation beams and a plurality of defocus-sensing beams.

* * * * *